United States Patent [19]

Jelich et al.

[11] Patent Number: 4,960,455

[45] Date of Patent: * Oct. 2, 1990

[54] HERBICIDAL TRIAZOLODIHYDROPYRIMIDINE-2-SULPHONAMIDES

[75] Inventors: Klaus Jelich; Peter Babczinski, both of Wuppertal; Hans-Joachim Santel, Leverkusen; Robert R. Schmidt, Bergisch-Gladbach; Harry Strang, Duesseldorf, all of Fed. Rep. of Germany

[73] Assignee: Bayer Aktiengesellschaft, Leverkusen, Fed. Rep. of Germany

[*] Notice: The portion of the term of this patent subsequent to Aug. 8, 2006 has been disclaimed.

[21] Appl. No.: 320,249

[22] Filed: Mar. 7, 1989

[30] Foreign Application Priority Data

Mar. 11, 1988 [DE] Fed. Rep. of Germany ....... 3808122

[51] Int. Cl.$^5$ ................. A01N 43/713; C07D 487/04
[52] U.S. Cl. ......................................... 71/92; 544/263
[58] Field of Search ............................ 544/263; 71/92

[56] References Cited

U.S. PATENT DOCUMENTS

| 4,144,330 | 3/1979 | Gsell et al. | 544/263 |
| 4,734,123 | 3/1988 | Monte | 71/92 |
| 4,854,964 | 8/1989 | Jelich et al. | 544/263 |
| 4,859,231 | 8/1989 | Westermann | 71/90 |
| 4,904,301 | 2/1990 | Pearson et al. | 544/263 |

FOREIGN PATENT DOCUMENTS

| 0142152 | 5/1985 | European Pat. Off. . |
| 0244948 | 11/1987 | European Pat. Off. . |
| 3539386 | 5/1987 | Fed. Rep. of Germany ...... 544/263 |
| 3627411 | 2/1988 | Fed. Rep. of Germany . |
| 3640155 | 5/1988 | Fed. Rep. of Germany ...... 544/263 |
| 951652 | 3/1964 | United Kingdom ............... 544/263 |

*Primary Examiner*—Donald G. Daus
*Attorney, Agent, or Firm*—Sprung Horn Kramer & Woods

[57] ABSTRACT

Herbicidal triazolodihydropyrimidine-2-sulphonamides of the formula

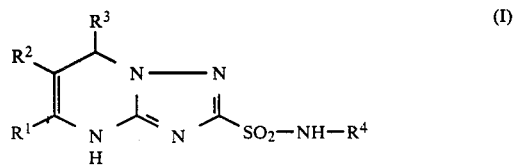

(I)

in which
$R^1$, $R^2$ and $R^3$ independently of one another each stand for hydrogen or for optionally substituted alkyl and
$R^4$ stands for in each case optionally substituted aryl or heteroaryl.

10 Claims, No Drawings

HERBICIDAL TRIAZOLODIHYDROPYRIMIDINE-2-SULPHONAMIDES

The invention relates to new triazolopyrimidine-2-sulphonamides, a process for their preparation and their use as herbicides.

It has been disclosed that certain triazolopyrimidine-2-sulphonamides, such as, for example, the compound 5,7-dimethyl-N-(2-methoxycarbonylphenyl)-1,2,4,-triazolo[1,5-a]-pyrimidine-2-sulphonamide possess herbicidal properties (cf., for example, U.S. Pat. No. 4,755,212 corresponding to EP No. 142,152).

However, the herbicidal activity of these previously known compounds against problem weeds and their tolerance towards important crop plants is not completely satisfactory in all fields of application.

New triazolopyrimidine-2-sulphonamides of the general formula (I)

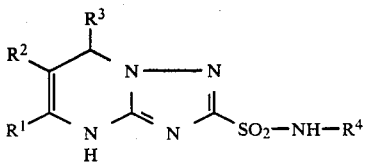

in which
R$^1$, R$^2$ and R$^3$ independently of one another each stand for hydrogen or for optionally substituted alkyl and
R$^4$ stands for in each case optionally substituted aryl or heteroaryl,
have now been found.

The compounds of the formula (I) are in equilibrium with the tautomeric compounds of the formula (Ia)

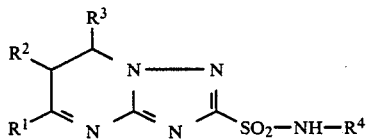

in which
R$^1$, R$^2$, R$^3$ and R$^4$ have the abovementioned meaning; compounds of the formula (I) and compounds of the formula (Ia), and also their mixtures, are embraced according to the invention.

Furthermore, it has been found that the new triazolo-pyrimidine-2-sulphonamides of the general formula

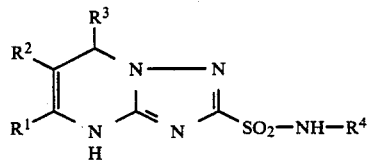

in which
R$^1$, R$^2$ and R$^3$ independently of one another each stand for hydrogen or for optionally substituted alkyl and
R$^4$ stands for in each case optionally substituted aryl or heteroaryl, and also their tautomers of the formula (Ia) are obtained in a process in which aminotriazolylsulphonamides of the formula (II)

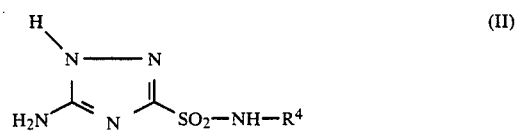

in which
R$^4$ has the abovementioned meaning, are reacted with keto alcohols of the formula (III)

in which
R$^1$, R$^2$ and R$^3$ have the abovementioned meaning, if appropriate in the presence of a diluent.

It has been found that the new triazolo-pyrimidine-2-sulphonamides of the general formula (I) possess herbicidal properties.

Surprisingly, the triazolo-pyrimidine-2-sulphonamides of the general formula (I) according to the invention show a considerably better herbicidal activity against problem weeds than the triazolpyrimidine-2-sulphonamide derivatives known from the prior art, such as, for example, 5,7-dimethyl-N-(2-methoxycarbonylphenyl)-1,2,4-triazolo[1,5-a]-pyrimidine-2-sulphonamide, which compounds are chemically similar and of a similar type of action.

Formula (I) provides a general definition of the triazolopyrimidine-2-sulphonamides according to the invention. Preferred compounds of the formula (I) are those
in which
R$^1$, R$^2$ and R$^3$ independently of one another each stand for hydrogen, for straight-chain or branched alkyl which has 1 to 4 carbon atoms, for straight-chain or branched halogenoalkyl which has 1 to 4 carbon atoms and 1 to 9 identical or different halogen atoms, for in each case straight-chain or branched alkoxyalkyl or alkylthioalkyl, each of which has 1 to 4 carbon atoms in the individual alkyl moieties, or for aryloxyalkyl or arylthioalkyl, each of which has 1 to 4 carbon atoms in the straight-chain or branched alkyl moiety and 6 to 10 carbon atoms in the aryl moiety and each of which is optionally substituted once or more than once in the aryl moiety by identical or different substituents, suitable substituents being: halogen, cyano, nitro, in each case straight-chain or branched alkyl, alkoxy or alkylthio, each having 1 to 4 carbon atoms, in each case straight-chain or branched halogenoalkyl, halogenoalkoxy or halogenoalkylthio, each having 1 to 4 carbon atoms and 1 to 9 identical or different halogen atoms, in each case straight-chain or branched alkoxycarbonyl or alkoximinoalkyl, each having 1 to 4 carbon atoms in the individual alkyl moieties, and phenyl which is optionally substituted once or more than once by identical or different substituents from the series comprising halogen and/or straight-chain or branched alkyl having 1 to 4 carbon atoms, and $R^4$ stands for aryl which has 6 to 10 carbon atoms and which is optionally substituted once or more than once by identical or different substituents, or for a 5- to 7-membered heterocyclic ring which has 1 to 3 hetero atoms, in particular nitrogen, oxygen and-/or sulphur, and which is optionally benzofused and/or substituted once or more than once by identical or different substituents, suitable substituents in each case being: fluorine, chlorine, bromine, iodine, cyano, nitro, hydroxyl, in each case straight-chain or branched alkyl, alkoxy, alkylthio, alkylcarbonyl, alkylsulphinyl or alkylsulphonyl, each having 1 to 6 carbon atoms, in each case straight-chain or branched halogenoalkyl, halogenoalkoxy, halogenoalkylthio, halogenoalkylsulphinyl, halogenoalkylsulphonyl or halogenoalkylcarbonyl, each having 1 to 6 carbon atoms and 1 to 9 identical or different halogen atoms, phenyl, phenoxy, phenylthio, phenylcarbonyl, hydroxycarbonyl, in each case straight-chain or branched alkoxycarbonyl, alkenyloxycarbonyl or alkoxyalkoxycarbonyl, each having 1 to 6 carbon atoms in the individual alkyl moieties and 3 to 6 carbon atoms in the alkenyl moiety, respectively, and also hydroximinoalkyl or straight-chain or branched alkoximinoalkyl, each having 1 to 4 carbon atoms in the individual alkyl moieties.

Particularly preferred compounds of the general formula (I) are those in which $R^1$, $R^2$ and $R^3$ independently of one another each stand for hydrogen, methyl, ethyl, n- or i-propyl, n-, i-, s- or t-butyl, for chloromethyl, dichloromethyl, trichloromethyl, fluoromethyl, difluoromethyl, trifluoromethyl, dichlorofluoromethyl, chlorodifluoromethyl or fluorochloromethyl, for methoxymethyl, ethoxymethyl, n- or i-propoxymethyl, methylthiomethyl, ethylthiomethyl, n- or i-propylthiomethyl or for phenoxymethyl or phenylthiomethyl each of which is optionally substituted once, twice or three times in the phenyl moiety by identical or different substituents, suitable substituents being: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, trifluoromethylthio, methoxycarbonyl, ethoxycarbonyl, methoximinomethyl, ethoximinomethyl, methoximinoethyl and ethoximinoethyl, or for phenyl which is optionally substituted once, twice or three times by identical or different substituents from the series comprising fluorine, chlorine, bromine, methyl and/or ethyl, and $R^4$ stands for phenyl or naphthyl, each of which is optionally substituted once, twice or three times by identical or different substituents, or for a heterocyclic ring of the formula

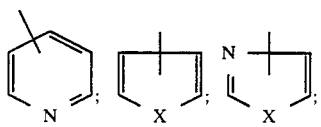

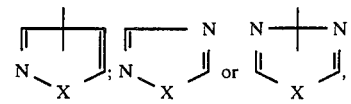

X in each case standing for oxygen, sulphur, an NH group or an N—CH$_3$ group, which ring is optionally benzo-fused and/or substituted once, twice or three times by identical or different substituents, suitable substituents for phenyl, naphthyl and the heterocyclic ring in each case being: fluorine, chlorine, bromine, iodine, cyano, nitro, hydroxyl, methyl, ethyl, n- or i-propyl, n-, i-, s- or t-butyl, methoxy, ethoxy, n- or i-propoxy, methylthio, ethylthio, acetyl, propionyl, methylsulphinyl, methylsulphonyl, trifluoromethyl, trifluoromethoxy, trifluoromethylthio, trifluoromethylsulphinyl, trifluoromethylsulphonyl, chloroacetyl, dichloroacetyl, trifluoroacetyl, phenyl, phenoxy, phenylthio, benzoyl, hydroxycarbonyl, methoxycarbonyl, ethoxycarbonyl, n- or i-propoxycarbonyl, allyloxycarbonyl, methoxymethoxycarbonyl, ethoxyethoxycarbonyl, hydroximinomethyl, methoximinomethyl, methoximinoethyl and ethoximinoethyl.

Very particularly preferred compounds of the general formula (I) are those in which $R^1$ and $R^3$ independently of one another stand for hydrogen, for methyl, ethyl, n- or i-propyl, n-, i-, s- or t-butyl, for methoxymethyl, ethoxymethyl, n- or i-propoxymethyl, for methylthiomethyl, for trifluoromethyl, trichloromethyl, dichlorofluoromethyl, chlorodifluoromethyl, for phenoxymethyl or phenylthiomethyl, $R^2$ stands for hydrogen and $R^4$ stands for phenyl, α-naphthyl or β-naphthyl, each of which is optionally substituted once, twice or three times by identical or different substituents, or for a heterocyclic ring of the formula

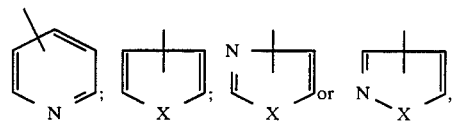

X in each case standing for oxygen, sulphur, an NH group or an N—CH$_3$ group, which ring is optionally benzo-fused and/or substituted once, twice or three times by identical or different substituents, suitable substituents for phenyl, naphthyl and the heterocyclic ring in each case being: fluorine, chlorine, bromine, iodine, cyano, nitro, hydroxyl, methyl, ethyl, methoxy, ethoxy, n- or i-propoxy, methylthio, acetyl, trifluoromethyl, trifluoromethoxy, trifluoromethylthio, phenyl, phenoxy, phenylthio, hydroxycarbonyl, methoxycarbonyl, ethoxycarbonyl, allyloxycarbonyl, ethoxyethoxycarbonyl, hydroximinomethyl, methoximinomethyl or methoximinomethyl.

Especially preferred compounds of the formula (I) are those in which $R^1$ stands for methyl or methoxymethyl, $R^2$ stands for hydrogen, $R^3$ stands for hydrogen, methyl or methoxymethyl and $R^4$ for phenyl which is optionally substituted once, twice or three times by identical or different substituents, suitable substituents being: fluorine, chlorine, bromine, cyano, nitro, hydroxyl, methyl, ethyl, methoxy, ethoxy, n- or i-propoxy, methylthio, acetyl, trifluoromethyl, trifluoromethoxy, trifluoromethylthio, phenyl, phenoxy, phenylthio, hydroxycarbonyl, methoxycarbonyl, ethoxycarbonyl, allyloxycarbonyl, ethoxyethoxycarbonyl, hydroximinomethyl, methoximinomethyl or methoximinoethyl.

The following triazolo-pyrimidine-2-sulphonamides of the general formula (I) may be mentioned individually in addition to the compounds mentioned in the Preparation Examples:

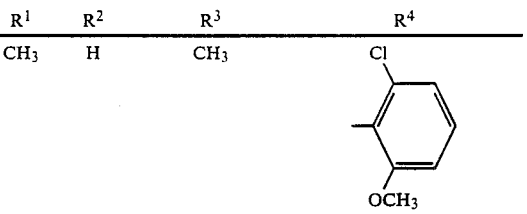

(I)

| $R^1$ | $R^2$ | $R^3$ | $R^4$ |
|---|---|---|---|
| $CH_3$ | H | $CH_3$ | 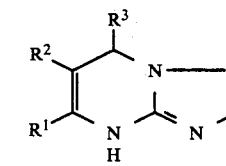 |
| $CH_3$ | H | $CH_3$ | 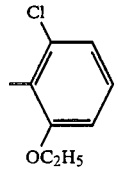 |
| $CH_3$ | H | $CH_3$ | 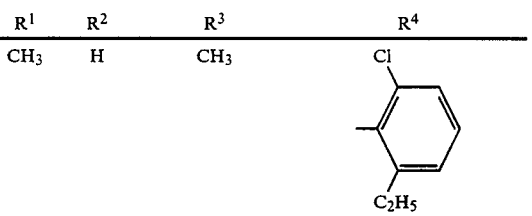 |
| $CH_3$ | H | $CH_3$ | 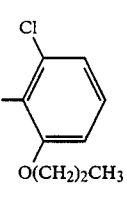 |
| $CH_3$ | H | $CH_3$ | 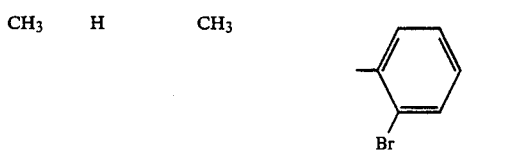 |
| $CH_3$ | H | $CH_3$ | 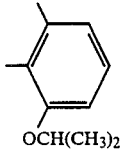 |
| $CH_3$ | H | $CH_3$ | 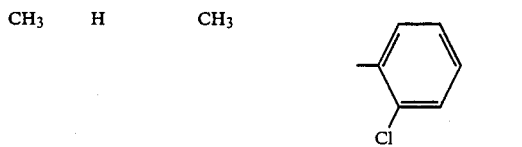 |
| $CH_3$ | H | $CH_3$ | 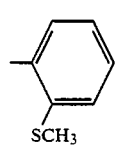 |
| $CH_3$ | H | $CH_3$ | 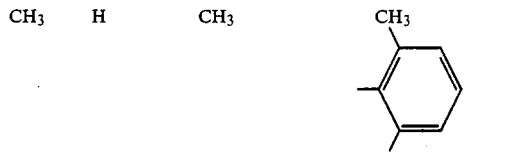 |
| $CH_3$ | H | $CH_3$ | 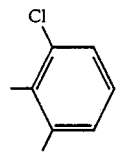 |
| $CH_3$ | H | $CH_3$ | 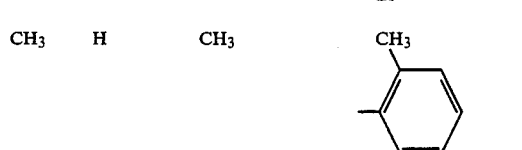 |
| $CH_3$ | H | $CH_3$ | 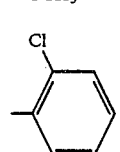 |
| $CH_3$ | H | $CH_3$ | 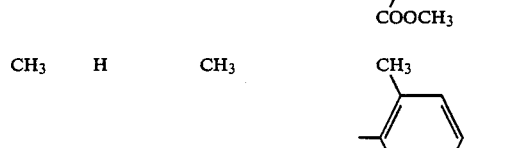 |
| $CH_3$ | H | $CH_3$ | 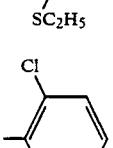 |
| $CH_3$ | H | $CH_3$ |  |
| $CH_3$ | H | $CH_3$ | 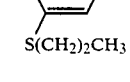 |

-continued $$\text{(I)}$$

Structure: R²-C(R¹)=C(R³)-N(-N=C(-SO₂-NH-R⁴)-N=)-NH with R¹ on carbon bearing NH

| R¹ | R² | R³ | R⁴ |
|---|---|---|---|
| CH₃ | H | CH₃ | 2-Cl, 6-SCH(CH₃)₂ phenyl |
| CH₃ | H | CH₃ | 2,6-diCl phenyl |
| CH₃ | H | CH₃ | 2-Cl, 6-Br phenyl |
| CH₃ | H | CH₃ | 2-Cl, 6-I phenyl |
| CH₃ | H | CH₃ | 2-Br, 6-OCH₃ phenyl |
| CH₃ | H | CH₃ | 2-Br, 6-OC₂H₅ phenyl |
| CH₃ | H | CH₃ | 2-SC₂H₅, 4-CH₃ phenyl |
| CH₃ | H | CH₃ | 2,6-diCl, 4-CH₃ phenyl |

-continued $$\text{(I)}$$

| R¹ | R² | R³ | R⁴ |
|---|---|---|---|
| CH₃ | H | CH₃ | 2-Cl, 5,6-diCH₃ phenyl |
| CH₃ | H | H | 2-Cl, 5-CH₃ phenyl |
| CH₃ | H | H | 2-Cl, 6-OCH₃ phenyl |
| CH₃ | H | H | 2-CH₃, 5-COOCH₃ phenyl |
| CH₃ | H | H | 2-Cl, 6-SCH₃ phenyl |
| CH₃ | H | H | 2,6-diCl phenyl |
| CH₃ | H | H | 2-Cl, 6-Br phenyl |
| CH₃ | H | H | 2-Cl, 6-I phenyl |

-continued $$\text{(I)}$$

Structure: triazoline with R1, R2, R3 substituents and SO2—NH—R4 group

| R¹ | R² | R³ | R⁴ |
|---|---|---|---|
| CH₃ | H | CH₃O—CH₂— | 2-Cl, 6-CH₃-phenyl |
| CH₃ | H | CH₃O—CH₂— | 2-Cl, 6-OCH₃-phenyl |
| CH₃ | H | CH₃O—CH₂— | 2-CH₃, 6-COOCH₃-phenyl |
| CH₃ | H | CH₃O—CH₂— | 2-Cl, 5-SCH₃-phenyl |
| CH₃ | H | CH₃O—CH₂— | 2,6-diCl-phenyl |
| CH₃ | H | CH₃O—CH₂— | 2-Cl, 6-Br-phenyl |
| CH₃ | H | CH₃O—CH₂— | 2-Cl, 6-I-phenyl |
| CH₃ | H | CH₃ | 2,6-di-CH₃-phenyl |
| CH₃ | H | CH₃ | 2,6-di-CH₃, 4-Cl-phenyl |
| CH₃ | H | CH₃ | 2,6-di-CH₃, 4-Cl-phenyl (isomer) |
| CH₃ | H | CH₃O—CH₂— | 2,6-di-CH₃-phenyl |
| CH₃ | H | CH₃O—CH₂— | 2,6-di-CH₃, 4-Cl-phenyl |
| CH₃ | H | CH₃O—CH₂— | 2,6-di-CH₃, 4-Cl-phenyl (isomer) |
| CH₃ | H | H | 2,4,6-tri-Cl-phenyl |

If, for example, 5-amino-3-(2,6-dichlorophenylaminosulphonyl)-1,2,4-triazole and pentan-4-ol-2-one are used as starting substances, the course of the reaction of the process according to the invention may be represented by the following equation:

$$H_2N-\text{triazole}-SO_2-NH-\text{(2,6-dichlorophenyl)} +$$

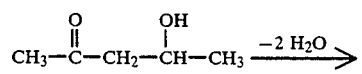

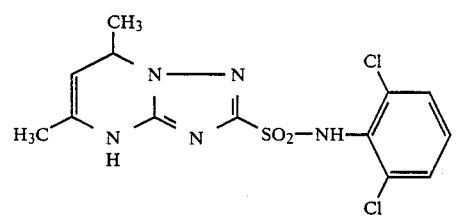

Formula (II) provides a general definition of the aminotriazolylsulphonamides required as starting substances for carrying out process (a) according to the invention. In this formula (II), $R^4$ preferably, or particularly preferentially, stands for those radicals which have already been mentioned in connection with the description of the substances of the formula (I) according to the invention as being preferred, or particularly preferred, for this substituent. In formula (II), $R^4$ very particularly preferentially stands for those radicals which have been mentioned in connection with the description of the substances of the formula (I) according to the invention as being very particularly preferred for these substituents.

Some of the aminotriazolylsulphonamides of the formula (II) are known (cf., for example, EP-A No. 244,844).

They are obtained in a process in which 3-amino-5-benzylthio-1,2,4-triazole of the formula (IVa)

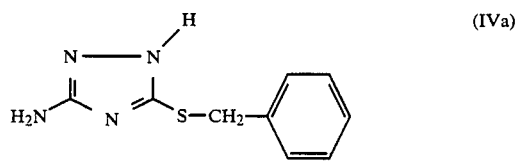

(cf., for example, J. Heterocycl. Chem. 12, 1187 [1975] or EP No. 142,152) which is present in a tautomeric equilibrium with the corresponding 5-amino-3-benzylthio compound of the formula (IVb)

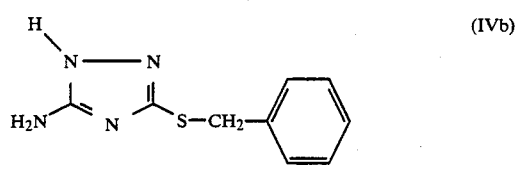

is initially reacted in a 1st step with phenyl chloroformate at temperatures between $-20°$ C. and $+20°$ C. in the presence of a diluent, such as, for example, pyridine, and the resulting 1-phenoxycarbonyl-3-benzylthio-5-amino-1,2,4-triazole of the formula (V)

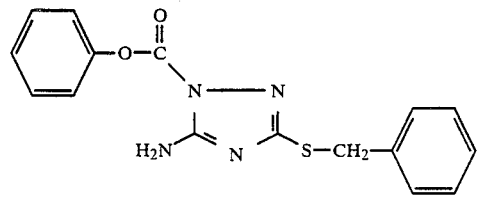

is reacted in a 2nd step with elemental chlorine at temperatures between $-20°$ C. and $+20°$ C. in the presence of water and in the presence of a diluent, such as, for example, chloroform, and in the presence of a reaction auxiliary, such as, for example, glacial acetic acid, and the 5-amino-1-phenoxycarbonyl-1,2,4-triazol-3-yl-sulphonyl chloride of the formula (VI)

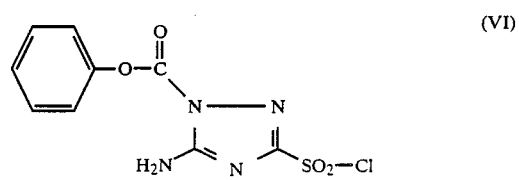

which can be obtained in this manner is reacted in a 3rd step with amines of the formula (VII)

in which $R^4$ has the abovementioned meaning, at temperatures between $0°$ C. and $60°$ C., if appropriate in the presence of a diluent, such as, for example, dichloromethane, and in the presence of an acid-binding agent, such as, for example, pyridine, and, if appropriate, in the presence of a reaction auxiliary, such as, for example, 4-dimethylaminopyridine, and then in a 4th step the phenoxycarbonyl protecting group in the 1-position of the triazole ring is eliminated from the resulting 5-amino-1-phenoxycarbonyl-1,2,4-triazol-3-yl-sulphonamides of the formula (VIII)

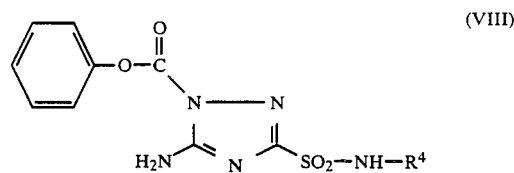

in which $R^4$ has the abovementioned meaning, by means of aqueous sodium hydroxide solution at temperatures between $0°$ C. and $40°$ C., if appropriate in the presence of a diluent, such as, for example, ethanol.

Amines of the formula (VII) are generally known compounds of organic chemistry.

Formula (III) provides a general definition of the keto alcohols furthermore required as starting substances for carrying out the process according to the invention. In this formula (III), $R^1$, $R^2$ and $R^3$ preferably stand for those radicals which have already been mentioned in connection with the description of the substances of the formula (I) according to the invention as being preferred for these substituents.

The keto alcohols of the formula (III) are generally known compounds or can be obtained in analogy to generally known processes.

Suitable diluents for carrying out the process according to the invention are inert organic solvents. Polar organic solvents, for example higher-boiling alcohols, such as ethylene glycol monoethyl ether, ethanol, propanol or butanol, or carboxylic acids, such as, for example, acetic acid, are particularly preferentially used.

When carrying out the process according to the invention, the reaction temperatures can be varied within a relatively wide range. In general, the process is carried out at temperatures between 20° C. and 200° C., preferably at temperatures between 50° C. and 150° C.

For carrying out the process according to the invention, 1.0 to 3.0 moles, preferably 1.0 to 2.0 moles, of keto alcohol of the formula (III) are generally employed per mole of aminotriazolylsulphonamide of the formula (II). The reaction is carried out, and the reaction products of the formula (I) are worked up and isolated by generally customary methods (cf. also the Preparation Examples).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantations and hopfields, and for the selective combating of weeds in annual cultures.

The compounds of the formula (I) according to the invention are particularly suitable for combating monocotyledon and dicotyledon weeds in monocotyledon crops, such as, for example, wheat, as a pre-emergence treatment and as a post-emergence treatment.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethyl-urea (METABENZTHIAZURON) for combating weeds in cereals; 4-amino-3-methyl-6-phenyl-1,2,4-triazin-5(4H)-one (METAMITRON) for combating weeds in sugar beets and 4-amino-6-(1,1-dimethylethyl)-3-methylthio-1,2,4-triazin-5(4H)-one (METRIBUZIN) for combating weeds in soy beans. Mixtures with 2,4-dichlorophenoxyacetic acid (2,4-D); 4-(2,4-dichlorophenoxy)-butyric acid (2,4-DB); 2,4-dichlorophenoxypropionic acid (2,4-DP); methyl 6,6-dimethyl-2,4-dioxo-3 [1-(2-propenyloxyamino)-butylidene]-cyclohexanecarboxylate (ALLOXYDIM); 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxybenzonitrile (BROMOXYNIL); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); 2-[4-(2,4-dichlorophenoxy)phenoxy]-propionic acid, its methyl ester or its ethyl ester (DICLOFOP); 4-amino-6-t-butyl-3-ethyl-thio-1,2,4-triazin-5(4H)-one (ETHIOZIN); 2-{4-[(6-chloro-2-benzoxazolyl)-oxy]-phenoxy}-propanoic acid, its methyl ester or its ethyl ester (FENOXAPROP); methyl 2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropyl-phenyl)-urea (ISOPROTURON); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-{[[((4-methoxy-6-methyl-1,3,5-triazin-2-yl)-amino)-carbonyl]-amino]-sulphonyl}-benzoic acid or its methyl ester (METSULFURON); N-(1-ethylpropyl)-3,4-dimethyl-2,6-dinitroaniline (PENDIMETHALIN); O-(6-chloro-3-phenylpyridazin-4-yl) S-octyl-thiocarbonate (PYRIDATE); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulphonyl]-thiophene-2-carboxylate (THIAMETURON); S-(2,3,3-trichloroallyl) N,N-diisopropylthiolcarbamate (TRIALLATE) and 3,5,6-trichloro-2-pyridyloxyacetic acid (TRICLOPYR) are also possible. Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

EXAMPLE 1

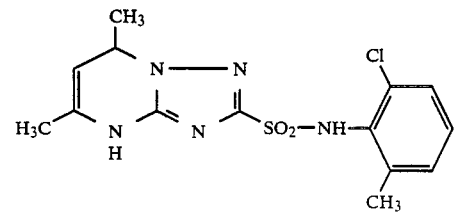

5 g (0.0174 mol) of 5-amino-3-(2-chloro-6-methylphenylaminosulphonyl)-1,2,4-triazole and 3.0 g (0.0294 mol) of pentan-4-ol-2-one (cf., for example, Chem. Ber. 100, 605 [1967]) are heated for 40 hours in 50 ml of dioxane under a nitrogen protective atmosphere at reflux temperature, the mixture is cooled and evaporated in vacuo, and the product was purified by chromatography (Silica gel; eluent: dichloromethane/acetone 4:1). The resulting solid was stirred with a small amount of ethyl acetate, filtered off with suction and dried.

1.8 g (30% of theory) of 5,7-dimethyl-N-(2-chloro-6-methylphenyl)-1,2,4-triazolo[1,5a][4H,7H]-dihydropyrimidine-2-sulphonamide of melting point 211° C.-214° C. are obtained.

The following triazolopyrimidine-2-sulphonamides of the general formula (I) are obtained in a corresponding manner and in accordance with the general instructions for the preparation:

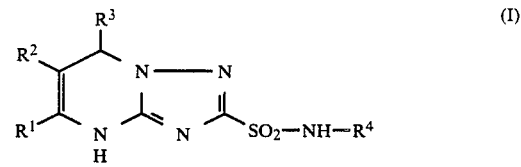

TABLE 1

| Example No. | $R^1$ | $R^2$ | $R^3$ | $R^4$ | Melting point/°C. |
|---|---|---|---|---|---|
| 2 | H | H | $CH_3$ | ![Cl, CH3 phenyl] | 240 |

TABLE 1-continued

| Example No. | R¹ | R² | R³ | R⁴ | Melting point/°C. |
|---|---|---|---|---|---|
| 3 | CH₃ | H | CH₃ | 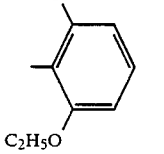 | 178 |
| 4 | CH₃ | H | CH₃ | 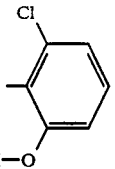 | 204 |

Preparation of the starting compounds

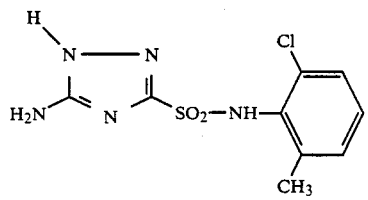

14.9 g (0.168 mol) of 45% strength aqueous sodium hydroxide solution are added to 34.1 g (0.0837 mol) of 5-amino-1-phenoxycarbonyl-1,2,4-triazol-3-yl-[N-(2-chloro-6-methyl-phenyl)]-sulphonamide in 350 ml of ethanol, and the mixture is stirred for one hour at room temperature, acidified with glacial acetic acid and evaporated in vacuo. The residue is washed three times with water and then dried at 80° C. in vacuo. The resulting solid is purified by stirring with diethyl ether.

13.5 g (56% of theory) of 5-amino-1,2,4-triazol-3-yl-[N-(2-chloro-6-methylphenyl)]-sulphonamide of melting point 217° C. are obtained.

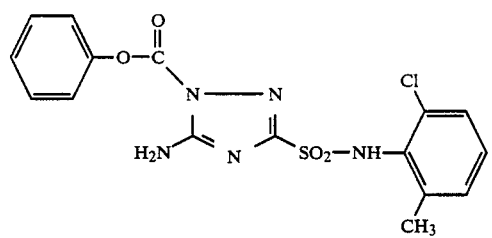

27.9 g (0.0922 mol) of 5-amino-1-phenoxycarbonyl-1,2,4-triazol-3-yl sulphochloride are added to 7.3 g (0.0922 mol) of absolute pyridine, 13 g (0.092 mol) of 2-chloro-6-methylaniline and 1.1 g (0.009 mol) of 4-dimethylaminopyridine in 300 ml of dry dichloromethane, the mixture is stirred for one hour at room temperature, the solvent is removed in vacuo, the oily residue is stirred with water, the aqueous phase is decanted off and the remaining oil is crystallized from ethanol.

35.5 g (95% of theory) of 5-amino-1-phenoxycarbonyl-1,2,4-triazol-3-yl-[N-(2-chloro-6-methylphenyl)]-sulphonamide of melting point 200° C. are obtained.

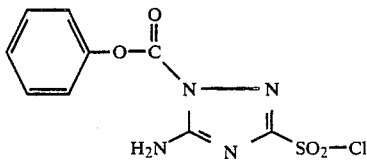

30 ml of glacial acetic acid and 15 ml of water are added to 136.6 g (0.419 mol) of 5-amino-1-phenoxycarbonyl-3-benzylthio-1,2,4-triazole in 1,700 ml of chloroform, and a stream of chlorine gas which has not been dried is passed through this suspension for one hour at −5° C., with a clear solution being formed. For working up, the solvent is removed in vacuo and the residue is stirred with 1 l of ether. The ether-insoluble solid is filtered off with suction and dried.

101 g (80% of theory) of 5-amino-1-phenoxycarbonyl-1,2,4-triazol-3-yl-sulphochloride of melting point 164° C. are obtained.

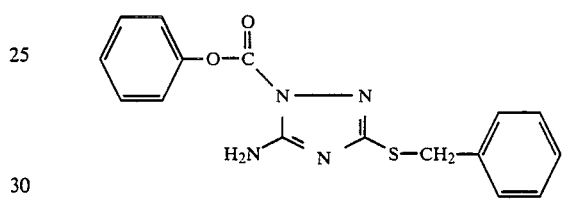

83.6 g (0.5339 mol) of phenyl chloroformate are added dropwise and with cooling to 100 g (0.4854 mol) of 3-amino-5-benzylthio-1,2,4-triazole (cf. J. Het. Chem. 12, 1187 [1975]) in 700 ml of absolute pyridine in a manner such that the internal temperature does not rise above 5° C. When the addition is complete, the mixture is stirred for 60 more minutes at 10° C., the reaction mixture is then poured into ice water, and the precipitated solid is filtered off with suction and recrystallized from ethanol.

140 g (88.5% of theory) of 5-amino-3-benzylthio-1-phenoxycarbonyl-1,2,4-triazole of melting point 285° C. (decomposition) are obtained.

Use Examples

In the following Use Examples, the compound listed below is employed as comparison substance:

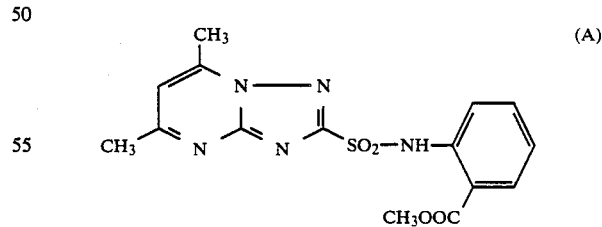

(A)

5,7-Dimethyl-N-(2-methoxycarbonyl-phenyl)-1,2,4-triazolo-[1,5-a]-pyrimidine-2-sulphonamide (disclosed in EP-A No. 142,152/compound 10)

Example A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, for example the compound according to Preparation Example (1) has a clearly superior herbicidal activity against monocotyledon and dicotyledon weeds compared with the comparison compound (A).

Example B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in damage in comparison to the development of the untreated control. The figures denote:

0%=no action (like untreated control)
100%=total destruction

In this test, for example the compound according to Preparation Example (1) shows a clearly superior herbicidal activity against monocotyledon and dicotyledon weeds compared with the comparison compound (A).

It is understood that the specification and examples are illustrative but not limitative of the present invention and that other embodiments within the spirit and scope of the invention will suggest themselves to those skilled in the art.

We claim:

1. A triazolodihydropyrimidine-2-sulphonamide of the formula

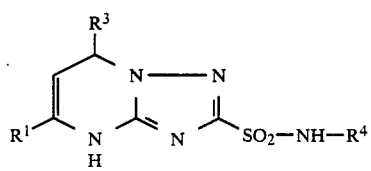

(I)

in which
R$^1$ is hydrogen or alkyl which has 1 to 4 carbon atoms,
R$^3$ is alkyl which has 1 to 4 carbon atoms or methoxymethyl, and
R$^4$ is unsubstituted or mono-, di- or trisubstituted phenyl, the substituents being identical or different and being selected from the group consisting of fluorine, chlorine, bromine, methyl, ethyl, n- or iso-propyl methoxy, ethoxy, n- or iso-propoxy, methoxycarbonyl, ethoxycarbonyl, methylthio, ethylthio and n- or iso-propylthio.

2. A triazolodihydropyrimidine-2-sulphonamide according to claim 1, in which
R$^1$ is hydrogen or methyl, and
R$^3$ is methyl.

3. A triazolodihydropyrimidine-2-sulphonamide according to claim 2, in which
R$^4$ is unsubstituted or mono-, di- or trisubstituted phenyl, the substituents being identical or different and being selected from the group consisting of fluorine, chlorine, methyl, ethyl, methoxy, ethoxy, n-propoxy and iso-propoxy.

4. A compound according to claim 1, wherein such compound is 5,7-dimethyl-N-(2-chloro-6-methylphenyl)-1,2,4-triazolo[1,5a][4H,7H]-dihydropyrimidine-2-sulphonamide of the formula

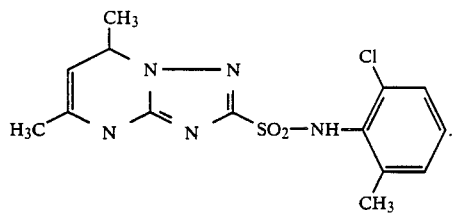

5. A compound according to claim 1, wherein such compound is 7-methyl-N-(2-chloro-6-methylphenyl)-1,2,4-triazolo[1,5a][4H,7H]-dihydropyrimidine-2-sulphonamide of the formula

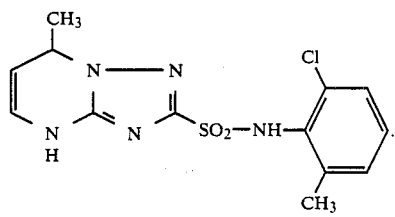

6. A compound according to claim 1, wherein such compound is 5,7-dimethyl-N-(2-chloro-6-ethoxyphenyl)-1,2,4-triazolo[1,5a][4H,7H]-dihydropyrimidine-2-sulphonamide of the formula

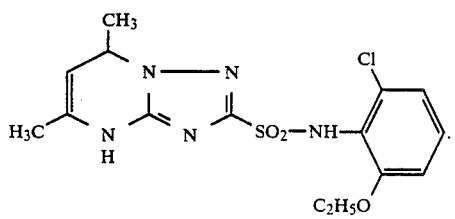

7. A compound according to claim 1, wherein such compound is 5,7-dimethyl-N-(2-chloro-6-isopropoxyphenyl)-1,2,4-triazolo[1,5a][4H,7H]-dihydropyrimidine-2-sulphonamide of the formula

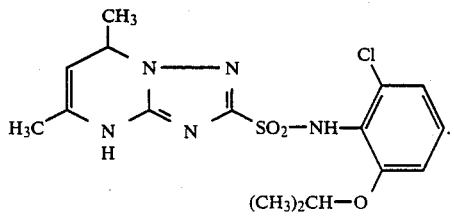

8. A herbicidal composition comprising a herbicidally effective amount of a compound according to claim 1 and a diluent.

9. A method of combating unwanted vegetation which comprises applying to such vegetation or to a locus from which it is desired to exclude such vegetation a herbicidal composition comprising a herbicidally effective amount of a compound according to claim 1.

10. The method according to claim 9, wherein such compound is
- 5,7-dimethyl-N-(2-chloro-6-methylphenyl)-1,2,4-triazolo[1,5a][4H,7H]-dihydropyrimidine-2-sulphonamide,
- 7-methyl-N-(2-chloro-6-methylphenyl)-1,2,4-triazolo[1,5a][4H,7H]-dihydropyrimidine-2-sulphonamide,
- 5,7-dimethyl-N-(2-chloro-6-ethoxyphenyl)-1,2,4-triazolo[1,5a][4H,7H]-dihydropyrimidine-2-sulphonamide or
- 5,7-dimethyl-N-(2-chloro-6-isopropoxyphenyl)-1,2,4-triazolo[1,5a][4H,7H]-dihydropyrimidine-2-sulphonamide.

* * * * *

UNITED STATES PATENT AND TRADEMARK OFFICE
CERTIFICATE OF CORRECTION

PATENT NO. : 4,960,455

DATED : October 2, 1990

INVENTOR(S) : Jelich et al.

It is certified that error appears in the above-identified patent and that said Letters Patent is hereby corrected as shown below:

Col. 20, line 31 Delete " 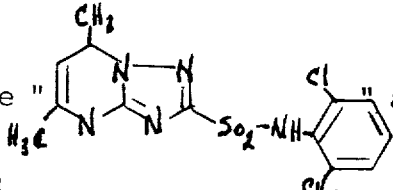 " and substitute

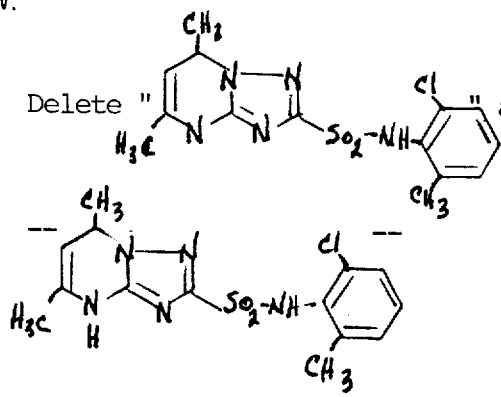

Signed and Sealed this

Seventeenth Day of November, 1992

*Attest:*

DOUGLAS B. COMER

*Attesting Officer*     *Acting Commissioner of Patents and Trademarks*